US006798518B2

United States Patent
DiFoggio et al.

(10) Patent No.: US 6,798,518 B2
(45) Date of Patent: Sep. 28, 2004

(54) METHOD AND APPARATUS FOR A DERIVATIVE SPECTROMETER

(75) Inventors: Rocco DiFoggio, Houston, TX (US); Arnold Walkow, Houston, TX (US); Paul Bergren, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 10/162,030

(22) Filed: Jun. 4, 2002

(65) Prior Publication Data

US 2003/0223069 A1 Dec. 4, 2003

Related U.S. Application Data

(60) Provisional application No. 60/385,633, filed on Jun. 4, 2002.

(51) Int. Cl.[7] ............................. G01J 3/51; G01N 21/27
(52) U.S. Cl. .................... 356/416; 356/419; 250/339.09
(58) Field of Search ................................. 356/416, 419; 250/339.07, 339.01, 339.12

(56) References Cited

U.S. PATENT DOCUMENTS

| RE28,216 E | 10/1974 | Barringer et al. ............. 356/93 |
| 4,326,802 A | 4/1982 | Smith, Jr. et al. ........... 356/316 |
| 4,590,374 A | 5/1986 | Brewster |
| 4,752,129 A | 6/1988 | Izumi et al. ................. 356/328 |
| 5,166,747 A | 11/1992 | Schroeder et al. ........... 356/326 |
| 5,426,297 A | 6/1995 | Dunphy et al. ......... 250/227.23 |
| 5,729,013 A | 3/1998 | Bergren, III ................. 250/255 |
| 5,939,717 A | 8/1999 | Mullins |
| 6,350,986 B1 | 2/2002 | Mullins et al. ........... 250/269.1 |
| 2002/0043620 A1 | 4/2002 | Tchakarov et al. |

FOREIGN PATENT DOCUMENTS

| EP | 0202585 | 11/1986 |
| GB | 2290139 | 12/1995 |

*Primary Examiner*—F. L. Evans
(74) *Attorney, Agent, or Firm*—Madan, Mossman & Sriram, P.C.

(57) ABSTRACT

The invention comprises a method of adapting derivative spectrometry for use in a downhole environment and addresses problems that are inherent in this environment. Such problems include, but are not limited to, elevated temperatures and scattering from particles residing within dirty fluid samples. The invention improves the resolution by measuring the first derivative of the spectrum. The derivative spectrometer of this invention operates by vibrating a linear variable interference filter back and forth along the plane of the filter or by oscillating a circular variable filter about some angle.

25 Claims, 2 Drawing Sheets

METHOD AND APPARATUS FOR A DERIVATIVE SPECTROMETER

CROSS REFERENCE TO RELATED APPLICATIONS

This application is related to and claims priority from U.S. patent application Ser. No. 10/162,023, entitled "A Method and Apparatus for a High Resolution Downhole Spectrometer" by Rocco DiFoggio, Paul Bergen and Arnold Walkow, filed on Jun. 4, 2002. This application is related to and claims priority from U.S. Patent Provisional Application No. 60/385,633, entitled "A Method and Apparatus for a Downhole Fluorescence Spectrometer" by Rocco DiFoggio, Paul Bergen and Arnold Walkow, filed on Jun. 4, 2002. This application is related to and claims priority from U.S. patent application Ser. No. 10/119,492 filed on Apr. 10, 2002 by Rocco DiFoggio et al., entitled "A Method and Apparatus for Downhole Refractometer And Attenuated Reflectance Spectrometer" which is hereby incorporated herein by reference in its entirety.

This application claims benefit to U.S. application 60/385,633 filed on Jun. 4, 2002.

BACKGROUND OF THE INVENTION

1. Field of the Invention

The present invention relates generally to the field of downhole sampling and in particular to derivative spectrometry in a downhole environment.

2. Summary of the Related Art

Oil companies take samples from potential hydrocarbon-bearing formations to determine a formation's propensity to produce hydrocarbons. Oil companies desire the most accurate measure of sample contamination percentage in real time as they are pumping fluid from a formation so that they can decide when to divert a sample being pumped to a sample collection tank. As formation fluid is pumped from the formation, the percentage of filtrate contained in the formation fluid sample diminishes in the pumped fluid. Thus, an oil company typically pumps until a pure sample, relatively free of filtrate can be obtained in order to accurately appraise the hydrocarbon producing potential of the surrounding formation. The oil company does not, however, want to pump unnecessarily long and waste very expensive rig time. Conversely, they do not want to pump too little and collect a useless sample, which is full of contaminants and does not reflect the properties of the formation fluid. If the contamination of filtrate contained in the sample is more than about 10%, the sample may be useless for its intended purpose. Moreover, it may not be discovered that the sample is useless until the sample is retrieved at the surface, making a return trip downhole necessary to collect another sample. In such cases, the PVT properties indicative of formation and formation fluid properties that are measured in the lab cannot be corrected back to true reservoir conditions because of excessive contamination. It is therefore desirable to perform sample contamination measurements downhole. One method of investigation is to use a spectrometer to perform optical measurements on the fluid samples collected in a downhole environment.

Numerous factors can affect downhole spectrometer measurements. In the downhole environment, photodetectors operate at high ambient temperatures and thus are very noisy and produce a substantially diminished signal. Also, contaminated samples consisting of flowing streams of crude oil containing scatterers such as sand particles or bubbles tend to add noise to the system. These scatterers cause the optical spectrum to momentarily "jump" up (get darker) as they pass through the sample cell. At high concentrations, these scatterers cause the measured spectrum to move or jump constantly. To first order, the effect of the scatters is just a momentary baseline offset. An operator can greatly improve the signal-to-noise ratio of a downhole spectrometer by modulating the wavelength of light and using a lock-in amplifier. Thus, there is a need for a spectrometer that operates in a downhole environment and diminishes the effects of the scatterers and the associated offsets.

Spectrometers typically disperse white light into constituent colors. The resulting rainbow of colors can be projected through a sample to be analyzed and onto a fixed array of photodetectors which sense light projected though the sample. Alternatively, by rotating a dispersive element (i.e. grating, prism), the rainbow can be mechanically scanned past a single photodetector one color at a time. In either case, an operator can obtain a sample's darkness versus wavelength, in other words, the sample's spectrum.

Photodetectors and their amplifiers always have some thermal noise and drift, which limit the accuracy of a spectral reading. As temperature increases, noise and drift increase dramatically higher at the same time that photodetector signal becomes significantly weaker. If an operator oscillates the wavelength (color) of light about some center wavelength, then the operator can reject most photodetector and amplifier noise and drift by using an electronic bandpass filter that passes only that electrical frequency at which the wavelength of light is being oscillated. The operator can further reject noise by using a phase-sensitive ("lock-in") amplifier that not only rejects signals that have the wrong frequency but also rejects signals that have the correct frequency but do not have a fixed phase relationship (indicative of noise) relative to the wavelength oscillation. A lock-in amplifier can improve signal to noise by as much as 100 db, which is a factor of $10^{100\ db/10}$ or 10 billion.

The output of the lock-in amplifier used in this procedure is proportional to the root-mean-square (RMS) amplitude of that portion of the total signal, which is at the same frequency and has a fixed phase relationship relative to the optical frequency being observed. The more that the darkness of the sample changes with color, the larger this RMS value will be. Thus, the output of lock-in amplifier for a system with an oscillating-wavelength input is proportional to the derivative of the spectrum (with respect to wavelength) at the center wavelength of the oscillation.

A spectrometer based on an oscillating-wavelength and a lock-in amplifier can be used to obtain high accuracy spectral measurements as described in the related art below. U.S. Pat. No. 4,070,111 entitled Rapid Scan Spectrophotometer, by Harrick, Jan. 24, 1978 discloses a spectrophotometer capable of rapid spectral scanning by mounting a low inertia reflective grating directly on the output shaft of a galvanometer-type optical scanner, and sweeping the beam dispersed from the grating across a spherical mirror and after reflection there from across a beam exit slit. The invention also describes rapid wavelength switching for a laser spectrometer.

U.S. Pat. No. 4,225,233 Rapid Scan Spectrophotometer, by Ogan Sep. 30, 1980 discloses a spectrometer capable of providing a predetermined wavelength of output light in accordance with a control voltage signal applied to a scanning element. The scanning element located at the grating image of the spectrometer is a small mirror attached to the rotor of a galvanometer. The angular position of the galvanometer is accurately controlled by a closed-loop electronic control. The spectrum reflected from the mirror is passed through a slit to provide the output light of a predetermined wavelength. Selection of the waveform of the control signal allows the spectrometer to be operated as a dual wavelength spectrometer, to use a linear wavelength scan, or other wavelength scan patterns for absorbance analyses of a sample.

U.S. Pat. No. 4,264,205 Rapid Scan Spectral Analysis System Utilizing Higher Order Spectral Reflections Of Holographic Diffraction Gratings, Landa Apr. 28, 1981 And U.S. Pat. No. 4,285,596 Holographic Diffraction Grating System For Rapid Scan Spectral Analysis, Landa, Aug. 25, 1981 discloses an improved optical system for rapid, accurate spectral analysis of the reflectivity or transmissivity of samples. A concave holographic diffraction grating oscillating at high speed provides a rapid scanning of monochromatic light through a spectrum of wavelengths. The rapid scan by the grating enables the reduction of noise error by averaging over a large number of cycles. It also reduces the measurement time and thus prevents sample heating by excessive exposure to light energy. A filter wheel is rotated in the optical path and is synchronous with the grating.

U.S. Pat. No. 4,968,122 Galvanometer Gimbal Mount, Hlousek et. al., Nov. 6, 1990 discloses an improved mounting in which a rotating diffraction grating assembly directly connects the grating to the galvanometer that rotates the grating. The galvanometer is gimbal-mounted on a plate so that its position, and that of the grating, can be adjusted so that the plane of dispersion of the grating passes through a desired point when the grating is rotated.

U.S. Pat. No. 4,969,739 Spectrometer With Direct Drive High Speed Oscillating Grating, McGee, Nov. 13, 1990 discloses an optical grating oscillating at a high rate to scan a narrow wavelength band of light through the spectrum dispersed by a grating. The grating is connected integrally with the rotor of a motor, which is energized to oscillate its rotor between selected limits. High-speed oscillation is achieved by driving the motor with a pulse modulator having a duty cycle controlled by the motor speed. The direction that the motor is driven is controlled by the polarity of the pulse-modulated signal applied to a winding of the motor. The limits of the oscillation of the grating and the rate of rotation of the grating between the limits are selectively variable.

U.S. Pat. No. 5,488,240 Apparatus And Method For Rotating An Optical Element Using A Moving Coil In A Constant Magnetic Field, Hlousek et al., Jan. 30, 1996 discloses an apparatus and method for rotating an optical element, such as a diffraction grating or mirror, utilizing a moving coil actuator and an optical encoder to provide precise element position control. The moving coil actuator, which is coupled to the optical element, is comprised of a coil immersed in a magnetic field created by a pair of magnets. Current flowing in the coil windings causes the coil, and ultimately the optical element, to rotate. An optical encoder monitors the rotation of the element and provides rotation signals representative of the instantaneous element position to an actuator control circuit. The actuator control circuit phase shifts the rotation signals and compares the phase shifted rotation signals to a desired reference signal to generate position and velocity error signals.

The grating and, possibly, additional optical elements direct the light to the sample or target of interest. The angular displacement of the diffraction grating relative to the incoming light beam can be closely correlated with the individual wavelengths or range of wavelengths at which the sample is to be analyzed. By controlling the angular rotation and position of the diffraction grating, a range of wavelengths can be scanned at a known rate over a known time interval and, consequently, the individual wavelengths can then be distinguished as a function of time.

U.S. Pat. No. 5,981,956 Systems And Methods For Detection Of Labeled Materials, Stem, Nov. 9, 1999 discloses a reciprocating radiation direction system comprising a mirror selected from one of a galvanometric mirror, angularly oscillating mirror, or a rotating polyhedral mirror for scanning a focused excitation radiation across a surface of a substrate at a rate of at least 20 image lines/second. Labeled targets on a support synthesized with polymer sequences at known locations can be detected by exposing marked regions of sample to radiation from a source and detecting the emission there from, and repeating the steps of exposition and detection until the sample is completely examined.

U.S. Pat. No. 5,963,320 Active spectrometer, Brooks, et. al. Oct. 5, 1999 discloses a grating spectrometer employing digital control of an oscillating component (a mirror) and phase-locked digital recording of the intensity profile within the narrow spectral domain defined by an oscillation frequency. Flexible choice of oscillation frequency permits measurement in a quiet region of the noise spectrum. Reference waveforms acquired with the same instrument can be stored and later used to de-convolute a more complex spectrum. The use of multiple detector/slit combinations along a Rowland circle makes the spectrometer sensitive to specific atomic elements. A claim is made for an apparatus for providing one or more electrical signals representing a measurement of spectral similarity between an emission spectrum from a light source and a reference spectrum. It comprises an optical instrument that spectrally disperses an optical signal, a driver that induces relative movement in the dispersion direction between the optical signal's imaged components in the image region and the template located in the image region, and a plurality of electro-optical sensors.

F. Vogt, U. Klocke, K. Rebstock, G. Schmidtke, V. Wander, M. Tack, Optical UV Derivative Spectrsocopy for Monitoring Gaseous Emissions, Applied Spectroscopy, November 1999, p. 1352. This paper's FIG. 2 shows an optical grating which is oscillating rapidly as it more slowly rotates about its axis. That is, the grating rapidly oscillates about each wavelength while it more slowly sweeps over a range of optical wavelengths. While known devices address derivative spectrometry in a laboratory environment, there is no known derivative spectrometer that is able to operate under the conditions of a downhole environment. Thus, there is a need for a derivative spectrometer that is able to operate under the conditions of a downhole environment.

SUMMARY OF THE INVENTION

The present invention comprises a method of adapting derivative spectroscopy for use in a downhole environment and addresses problems that are inherent in this environment. Such problems include, but are not limited to, elevated temperatures and scattering from particles or other scatterers residing within dirty fluid samples. Elevated temperatures reduce the photodetector response for the same light level. Scatterers cause momentary jumps or spikes in the spectra, which, to first order, are simply temporary baseline offsets. Such repeated offsets make it difficult to obtain quantitative absorbance spectra of the pure (scatterer-free) fluid except by taking the first derivative with respect to wavelength, which removes baseline offsets. The present invention improves the photometric resolution by measuring the first derivative of the spectrum.

In the present invention, the spectrometer's wavelength discrimination is provided by an optical filter whose color changes from one portion of the filter to another. By mechanically oscillating such a filter relative to one or more photodetectors, the amplitude of the signal produced by a photodetector will be proportional to the rate of change of the light transmission with wavelength (the first derivative spectra).

The derivative spectrometer of the present invention can operate by translation or vibration of a linear variable optical interference filter, back and forth along the plane of the filter. Alternatively, it can operate by rotational oscillation of a circular variable interference filter about some angle. The light can be filtered before entering the sample. Alternatively, we can let white light impinge on the sample, and filter the exiting light. In either case, the wavelength of light that eventually reaches the photodetector is oscillating. In a preferred embodiment, a vibrating actuator is provided to achieve the required oscillations about a given wavelength. Derivative spectrometry provides a higher resolution spectral measurement than normal methods of spectrometry. Through improved resolution, it is possible to accurately estimate the contamination percentage of a crude oil sample in real time as it is being pumped from the formation. (See co-pending applications Ser. No. 10/229,228 filed on Aug. 27, 2002 which is based on provisional application serial No. 60/359,895 both of which are incorporated herein by reference and U.S. patent application Ser. No. 10/119,492 filed on Apr. 10, 2002 by Rocco DiFoggio et al. entitled "A Method and Apparatus for Downhole Refractometer And Attenuated Reflectance Spectrometer" which is hereby incorporated herein by reference in its entirety.) Furthermore, the present invention enables determination of whether a contamination percentage is leveling off over time. High-resolution spectra provided by the present invention enables an improved estimation of the percentages of methane (natural gas), aromatic, olefins, saturates, and other crude oil properties. The present invention enables higher-resolution spectral measurements to determine a percentage contamination for samples and estimation of crude oil properties derived from the samples.

The present invention directly measures the derivative of the spectra, thereby minimizing baseline offset effect associated with scattering of light by contaminants found in the sample. Scattering, which can cause substantial baseline offsets, is particularly problematic for fluids withdrawn from unconsolidated formations. Such formations produce many fine particles that act as scatterers in a sample containing the particles. The present invention enables obtaining the first derivatives with respect to wavelength, which eliminates baseline offsets. These and other features and advantages of the present invention will be evident from reading the following description and figures for the present invention.

DETAILED DESCRIPTION OF THE INVENTION

Figure 1:
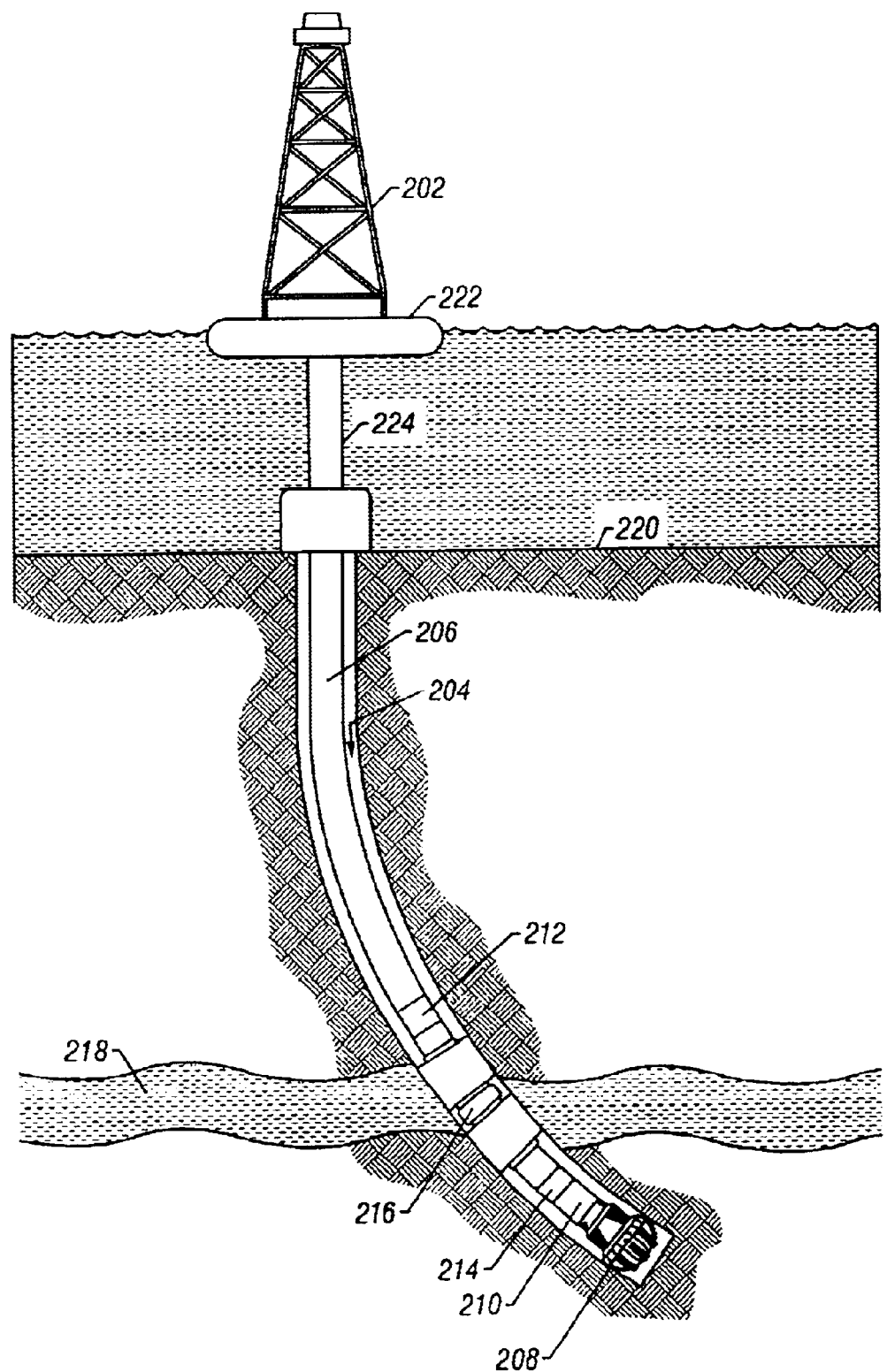
FIG. 1 is an illustration of the present invention in a downhole installation.

FIG. 1 illustrates a preferred embodiment of the present invention deployed in a borehole. The present invention is suitable for deployment in either a wire line, slick line or monitoring while drilling environment. FIG. 1 illustrates a preferred embodiment of the present invention deployed in a monitoring while drilling operation.

Turning now to FIG. 1, FIG. 1 is a drilling apparatus according to one embodiment of the present invention. A typical drilling rig 202 with a borehole 204 extending there from is illustrated, as is well understood by those of ordinary skill in the art. The drilling rig 202 has a work string 206, which in the embodiment shown is a drill string. The drill string 206 has attached thereto a drill bit 208 for drilling the borehole 204. The present invention is also useful in other types of work strings, and it is useful with a wireline, jointed tubing, coiled tubing, or other small diameter work string such as snubbing pipe. The drilling rig 202 is shown positioned on a drilling ship 222 with a riser 224 extending from the drilling ship 222 to the sea floor 220. However, any drilling rig configuration such as a land-based rig may be adapted to implement the present invention.

If applicable, the drill string 206 can have a downhole drill motor 210. Incorporated in the drill string 206 above the drill bit 208 is a typical testing unit, which can have at least one sensor 214 to sense downhole characteristics of the borehole, the bit, and the reservoir, with such sensors being well known in the art. A useful application of the sensor 214 is to determine direction, azimuth and orientation of the drill string 206 using an accelerometer or similar sensor. The bottom hole assembly (BHA) also contains the formation test apparatus 216 of the present invention, which will be described in greater detail hereinafter. A telemetry system 212 is located in a suitable location on the work string 206 such as above the test apparatus 216. The telemetry system 212 is used for command and data communication between the surface and the test apparatus 216.

Figure 2:
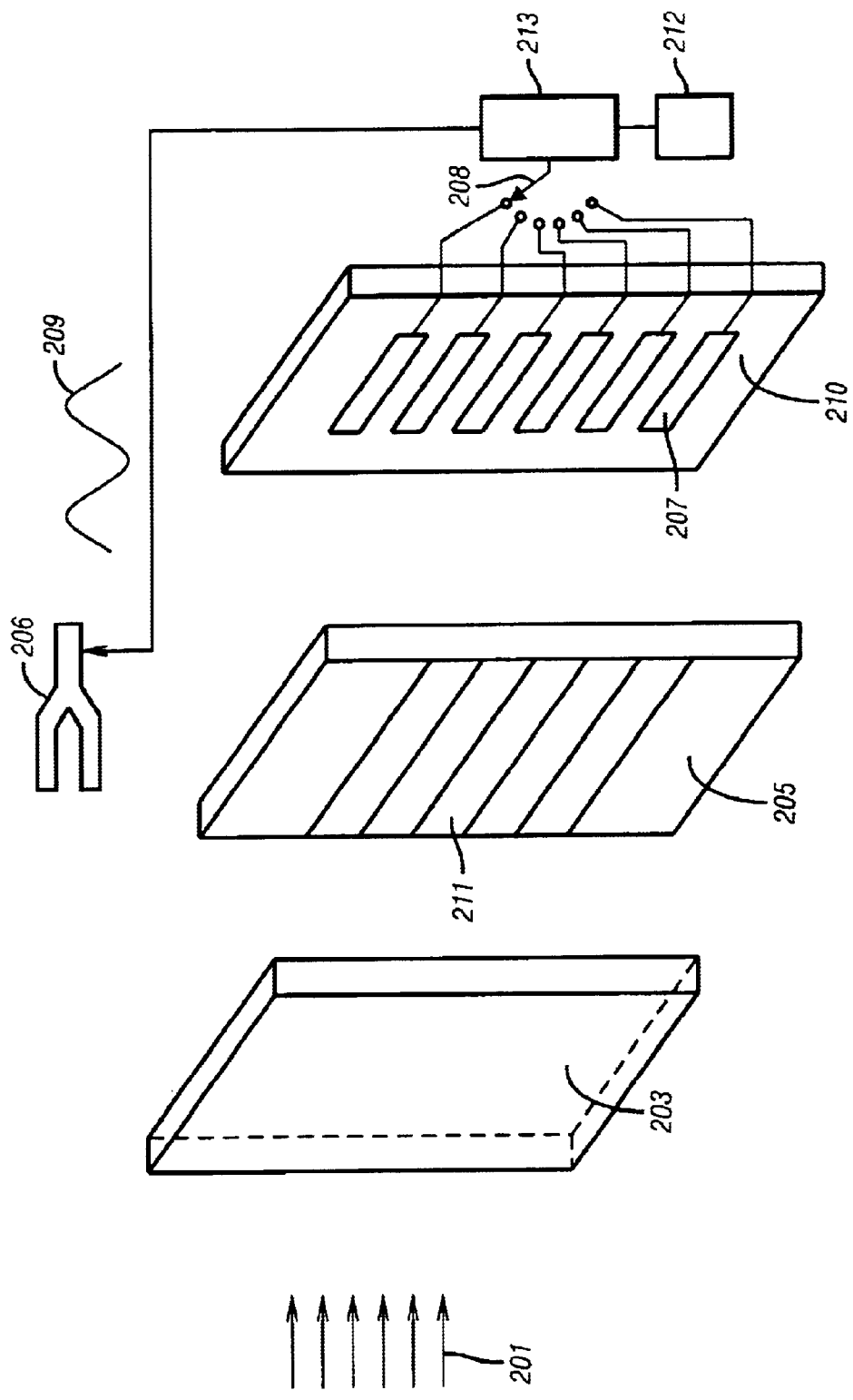
FIG. 2 is an illustration of a preferred embodiment of the present invention.

FIG. 2 illustrates a preferred embodiment of this invention. The present invention provides a linear variable filter 205, that is, a filter whose color bands 211 or color will change linearly from one end of the filter 205 to the other. In practice, linear variable filters are usually prepared by cutting them from the rim of a circular variable filter. Both linear and circular variable filters are suitable in a preferred embodiment. In both cases, the present invention provides an optical filter whose transmission wavelength varies from one portion of the filter to another. Thus, a variable optical filter, such as a linear variable or circular variable filter is used in a preferred embodiment to encounter light from the sample.

In a preferred embodiment, light 201 from a collimated light source 201 is directed so that it is incident upon or shown through a sample within sample chamber 203. The linear variable filter 205 is vibrated or reciprocally translated by vibrator 206 at an acoustic range frequency (e.g., 20–20,000 Hz) parallel to the plane of the linear filter while the filter situated above a photodetector array 207. The acoustic frequency of vibration 206 is used as a reference to track the motion of the linear variable filter and to eliminate all signals that are not at the same frequency as the reference signal 206 and are not fixed in phase relative to reference signal 206. Light 201 that passes through the sample 203 therefore is filtered over a small range of frequencies centered around the optical frequency. In a preferred embodiment of the invention, a vibrating actuator 206, for example a tuning fork or a piezoelectric actuator vibrates the linear variable filter 205.

In a preferred embodiment, a piezoelectric element alone, without a tuning fork 206, is a provided as a vibration source. The addition of a tuning fork still requires provision of a external exciter such as an electromagnetic coil or a piezoelectric element anyway. The piezoelectric element can be excited directly by an alternating electric current. Furthermore, it is noted that in a preferred embodiment, in order to obtain a sufficiently-recoverable signal amplitude, the amplitude of vibration should be 50–100% of the distance between the centers, referred to as the "pitch" of adjacent photodetector elements 207 in the photodetector array 210. The pitch is typically 25 to 200 microns. A single piezoelectric transducer typically would provide insufficient vibration amplitude, typically only 1–2 microns for the intended purpose of the present invention. Therefore, the preferred vibration source is a piezoelectric actuator, comprising either a bender plate, having up to 2 mm amplitude motion/deflection range or a stack of piezoelectric transducers, having up to 100 microns amplitude of total motion.

Each photodetector comprising the array 210 is connected to a lock-in amplifier 213, preferably through a low-gain preamplifier, which acts as a buffer to a multiplexer and a multiplexer 208. The lock-in amplifier output for all photodetectors in the array is plotted against wavelength, thus, it is possible to obtain a first derivative of the spectrum with respect to wavelength. The reference signal 209 as well as control and processing for the present invention are provided by processor 212. Processor 212 includes memory and input/output capability.

Obtaining the first derivatives with respect to wavelength substantially eliminates baseline offsets. Thus, the present invention can provide real-time oil-based mud contamination percentage. Accurate sample contamination percentage is a highly sought after sample parameter that oil companies require for accurate formation productivity assessment. Simulation studies show that the present invention could enable accurate correlation of the percentages of oil-based mud contamination, regardless of the crude oil type or the filtrate type, to high-resolution spectra over the fundamental hydrocarbon band region (3125–2855 cm−1) and, by inference, could provide similar correlation to the overtones (1550–1800 nanometers) of these fundamentals. The correlation is provided by a neural network or chemometric derived equations, discussed below, which are implemented either in processor 212 or by a processor on the surface (not shown).

The present invention provides high-resolution spectral measurements that are much more accurate and also provides robust correlation equations for estimating the percentages of methane (natural gas), aromatics, olefins, saturates, and other crude oil properties through chemometrics or a neural network. These correlation equations can be independent of the crude oil or filtrate involved.

In a preferred embodiment, the present invention uses chemometric derived equations or a neural network to determine the amount of aromatics, olefins, saturates and contaminants in a sample analyzed by the present invention based on spectral measurements. In known sampling techniques there is no direct measurement of a percent or level of contamination in a sample. The present invention provides a training set of known samples and utilizing chemometrics enables a computer to determine a mathematical expression for a percentage of aromatics, olefins, saturates and contaminants based on the spectrum measured for a sample. Chemometrics also eliminates the need to know what each spectral peak represents and how much a particular peak overlaps another peak. For example, the present invention can be utilized to determine a percent of contaminants based on a chemometric formula derived from a set of known samples for which the percentages of aromatics, olefins, and so on, have been measured by independent means. The training set can also be used to train a neural network to predict or determine the percent of aromatics, olefins, saturates and contaminants present in a sample.

The foregoing example of a preferred embodiment is intended for exemplary purposes only and is not intended to limit the scope of the invention, which is defined by the following claims.

What is claimed is:

1. A downhole spectrometer comprising:
   a sonde containing a spectrometer for traversing a bore hole, the spectrometer comprising:
      a collimated light source for illuminating a sample;
      a sample chamber for containing the sample;
      a variable filter having a an average wavelength centered about an absorption peak of the sample, to encounter light from the sample;
      a vibrating actuator attached to the variable filter for moving the variable filter; and
      a photodetector array for sensing light passing through the variable fitter.

2. The spectrometer of claim 1, further comprising:
   a multiplexor attached to the photodetector array for multiplexing individual photodetector outputs.

3. The spectrometer of claim 1,
   a vibration reference signal which is fixed in phase relative to the vibrating actuator.

4. The spectrometer of claim 1, further comprising:
   a lock-in amplifier for amplifying that portion of an output of each element of the photodetector array which is at a vibration frequency and in phase with a vibration reference signal.

5. The spectrometer of claim 1, further comprising:
   a neural network for predicting a property of the sample from a measured spectrum.

6. The spectrometer of claim 1, wherein the vibration actuator further comprises a piezoelectric device.

7. The spectrometer of claim 1, wherein the vibration actuator further comprises a stack of piezoelectric devices.

8. The spectrometer of claim 1, wherein the vibration actuator further comprises a bender device.

9. The spectrometer of claim 1, further comprising:
   an electronic band pass filter centered about a chemical absorption peak of the sample which rejects electrical noise outside the band of the electronic band pass filter.

10. The apparatus of claim 1, further comprising:
    an amplitude of vibration equal to a substantial fraction of the distance between centers of adjacent photodetectors.

11. The apparatus of claim 1, further comprising:
    a processor for producing a plot of spectrum versus wavelength to obtain a first derivative of the spectrum with respect to wavelength.

12. The spectrometer of claim 1, further comprising:
    a chemometric equation associated with a processor for predicting a property of the sample from the measured spectrum.

13. The spectrometer of claim 11, wherein the vibration actuator further comprises a bender device.

14. A method for downhole spectrometetry comprising:
    traversing a borehole with a sonde containing a spectrometer;
    containing a sample in a sample chamber;

illuminating the sample with a collimated light source;
passing light from the sample through a variable filter;
moving the variable filter; and
sensing light passing through the variable filter with a photodetector.

15. The method of claim 14, further comprising:
multiplexing individual photodetector outputs.

16. The method of claim 14, further comprising:
amplifying a portion of an output of the photodetector which is fixed in phase with respect to a vibrating actuator.

17. The spectrometer of claim 14, further comprising:
predicting in a neural network, a property of the sample from a measured spectrum.

18. The method of claim 14, further comprising:
vibrating the variable filter with a piezoelectric device.

19. The method of claim 14, further comprising:
vibrating the variable filter with a stack of piezoelectric devices.

20. The method of claim 14, further comprising:
vibrating the variable filter with a bender device.

21. The method of claim 14, further comprising:
aligning the variable filter relative to the photodetector so that an average wavelength striking the photodetector corresponds to a chemical absorption peak for the sample; and scanning in wavelengths over the chemical absorption peak by mechanically oscillating the variable filter.

22. The method of claim 14, further comprising:
vibrating a linear variable filter by an amplitude which is a substantial fraction of a distance between centers of the photodetector and an adjacent photodetectors.

23. The method of claim 14, further comprising:
plotting a spectrum versus wavelength to obtain a first derivative of the spectrum with respect to wavelength.

24. The method of claim 14, further comprising:
predicting a property of the sample from a measured spectrum from a chemometric equation.

25. The method of claim 14, further comprising:
exciting a piezoelectric device to vibrate the variable filter.

* * * * *